United States Patent [19]

Kresge et al.

[11] Patent Number: 4,547,605
[45] Date of Patent: Oct. 15, 1985

[54] CATALYST FOR ALKYLATION OF AROMATIC HYDROCARBONS

[75] Inventors: Charles T. Kresge, Sewell; John P. McWilliams, Woodbury, both of N.J.; James C. Vartuli, West Chester, Pa.; Michael P. Nicoletti, Turnersville, N.J.

[73] Assignee: Mobil Oil Corporation, New York, N.Y.

[21] Appl. No.: 536,469

[22] Filed: Sep. 28, 1983

[51] Int. Cl.[4] .............................................. C07C 2/68
[52] U.S. Cl. .................................................... 585/467
[58] Field of Search ........................................ 585/467

[56] References Cited

U.S. PATENT DOCUMENTS

| 3,130,007 | 4/1964 | Breck | 423/328 |
|---|---|---|---|
| 4,100,217 | 7/1978 | Young | 585/467 |
| 4,397,825 | 8/1983 | Whittem | 423/277 |

Primary Examiner—Curtis R. Davis
Attorney, Agent, or Firm—A. J. McKillop; M. G. Gilman; L. P. Hobbes

[57] ABSTRACT

This specification discloses a process for the alkylation of aromatics utilizing ZSM-23 catalyst. A particularly preferred embodiment utilizes ZSM-23 made from a forming mixture containing amorphous precipitated silica, as a silica source, including trace amounts of alumina and sodium chloride.

9 Claims, No Drawings

CATALYST FOR ALKYLATION OF AROMATIC HYDROCARBONS

BACKGROUND OF THE INVENTION

1. Field of the Invention

This invention relates to a process for the alkylation of an aromatic hydrocarbon by reaction with an olefin in the presence of ZSM-23 catalyst.

2. Description of the Prior Art

Alkylation of aromatic hydrocarbon compounds employing certain crystalline aluminosilicate zeolite catalysts is known in the art. For instance, U.S. Pat. No. 3,251,897 describes liquid phase alkylation in the presence of crystalline aluminosilicates such as faujausite, heulandite, clinoptilite, mordenite, dachiardite, zeolite X and zeolite Y. U.S. Pat. No. 2,904,607 shows alkylation of hydrocarbon compounds in the presence of crystalline metallic aluminosilicates, such as, magnesium aluminosilicate. The use of certain shape selective catalysts which have improved aging properties is taught in U.S. Pat. No. 3,751,506. U.S. Pat. No. 4,107,224 is specifically drawn to the manufacture of ethylbenzene by alkylating benzene with ethylene in the presence of certain shape-selective catalysts such as ZSM-5 under specified reaction conditions.

While the latter type catalysts represent a distinct improvement over previously suggested crystalline aluminosilicate catalysts particularly with respect to improved aging properties, they have the disadvantage of producing unwanted quantities of impurities along with the desired alkyl aromatic product, thereby decreasing the overall yield and selectivity for such product.

Thus, in the alkylation of benzene with ethylene, while desired ethylbenzene is the major product, small amounts of di- and possibly triethylbenzenes are always produced simultaneously with ethylbenzene, such amounts depending on the conversion of benzene to ethylbenzene. The polyethylbenzenes formed can be recycled to the alkylation zone, where they undergo transalkylation with benzene to produce more ethylbenzene. Alternatively, the polyethylbenzenes can be transalkylated with benzene in a separate reactor. The formation of polyethylbenzenes hence does not constitute an ultimate loss of the alkylating agent, ethylene. On the other hand, aromatic compounds other than ethyl- and polyethylbenzenes, that are formed during the alkylation reaction generally referred to as by-products, result in an irreversible loss of ethylene and cause difficulties in the product purification. By-products produced during ethylation of benzene include, for example, toluene, xylenes, cumene, n-propylbenzene, ethyltoluene, butylbenzene and other $C_{10}{}^+$ aromatics, the majority being $C_7$–$C_9$ aromatics. The formation of these by-products is increased when the benzene conversion to ethylbenzene is high.

$C_9{}^+$ aromatic by-products from the alkylation of benzene with ethylene in the presence of shape-selective catalysts such as ZSM-5 zeolite catalysts, result from the formation of transalkylation intermediates. Such transalkylation by-products which include polyethylbenzenes and polycyclic aromatics, not only degrade the ethylbenzene product purity but accelerate the catalyst aging rate as well when these by-products become part of the recycle feed to the reactor.

In the past, efforts have been made to prevent the formation of the relatively bulky transalkylation intermediates by reducing the effective pore size of the ZSM-5 zeolite. U.S. Pat. No. 3,906,054, for example, discloses a method for reducing the effective pore size of ZSM-5 zeolite by incorporating a small amount of phosphorous with the crystal structure.

SUMMARY OF THE INVENTION

It has now been found that formation of $C_9{}^+$ residue products transalkylation reactions can be inhibited in the alkylation of aromatics by employing ZSM-23 zeolite catalyst which has a slightly smaller pore diameter than ZSM-5 (4.5×5.6 A versus 4.8×7.1 A). Because of the reduced pore size of ZSM-23 relative to ZSM-5, the transalkylation intermediates of undesired $C_9{}^+$ aromatics are prevented from forming in processes utilizing ZSM-23. This results in a significant increase in ethylbenzene selectivity. It has also been found that the catalyst activity of ZSM-23 employed in the alkylation of aromatics is significantly increased where ZSM-23 is made from a non-gel forming mixture which contains an amorphous precipitated silica such as Hi-Sil. Commonly assigned, co-filed, U.S. patent application, Ser. No. 536,471, incorporated herein by reference, teaches the use of such ZSM-23 materials in xylene isomerization processes.

Zeolitic materials, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of small cavities which may be interconnected by a number of still smaller channels or pores. These cavities and pores are uniform in size within a specific zeolitic material. Since the dimensions of these pores are such as to accept for adsorption molecules of certain dimensions while rejecting those of larger dimensions, these materials have come to be known as "molecular sieves" and are utilized in a variety of ways to take advantage of these properties.

Zeolites, both natural and synthetic, include a wide variety of positive ion-containing crystalline materials such as aluminosilicates. These materials can be described as a rigid three-dimensional framework of $XO_4$ and $YO_4$ wherein X is silicon and/or germanium, and Y is one or more of aluminum, gallium, iron, chromium, vanadium, molybdenum, arsenic, manganese, or boron. This framework is comprised of tetrahedra which are cross-linked by the sharing of oxygen atoms whereby the ratio of the total Y and X atoms to oxygen atoms is 1:2. The electrovalence of the tetrahedra containing Y is balanced by the inclusion in the crystal of a cation, for example an alkali metal or an alkaline earth metal cation. This can be expressed wherein the ratio of Y atoms to the number of various cations, such as Ca/2, Sr/2, Na, K or Li, is equal to unity. One type of cation may be exchanged either entirely or partially with another type of cation utilizing ion exchange techniques in a conventional manner. By means of such cation exchange, it has been possible to vary the properties of a given material by suitable selection of the cation. The spaces between the tetrahedra are occupied by molecules of water prior to dehydration.

The crystalline zeolites utilized by the method of the present invention are members of a special class of zeolitic materials which exhibit unusual properties. Although these zeolites have unusually low Y atom contents, i.e. high X to Y mole ratios, e.g., high silica to alumina mole ratios, they are very active even when the X to Y mole ratio exceeds 30. The activity is surprising, since catalytic activity is generally attributed to framework Y atoms such as aluminum and/or cations associated with these atoms. These zeolites retain their crystallinity for long periods in spite of the presence of steam at high temperatures which induces irreversible collapse of the framework of other zeolites, e.g. of the X and A type. Furthermore, carbonaceous deposits, when formed, may be removed by burning at higher than usual temperatures to restore activity. These zeolites, used as catalysts, generally have low coke-forming activity and therefore are conducive to long times on stream between regenerations by burning carbonaceous deposits with oxygen-containing gas such as air.

An important characteristic of the crystal structure of this particular class of materials is that it provides a selective constrained access to and egress from the intracrystalline free space by virtue of having an effective pore size intermediate between the small pore Linde A and the large pore Linde X, i.e., the pore windows of the structure are of about a size such as would be provided by 10-membered rings of silicon atoms interconnected by oxygen atoms.

The catalyst useful in this invention is known as ZSM-23. The ZSM-23 composition has a characteristic X-ray diffraction pattern, the values of which are set out in Table I, below. The ZSM-23 zeolite composition, for the purpose of the present invention can also be identified, in terms of mole ratios of oxides and in the anhydrous state, as follows:

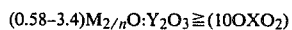

$$(0.58-3.4)M_{2/n}O:Y_2O_3 \geq (100XO_2)$$

wherein M is at least one cation having a valence n, X is silicon and/or germanium, and Y is one or more of aluminum, gallium, iron, chromium, vanadium, molybdenum, arsenic, manganese, or boron. A particularly preferred form of ZSM-23 is the aluminosilicate form wherein Y is aluminum and X is silicon.

Another preferred synthesized form of ZSM-23 zeolite has a formula, in terms of mole ratios of oxides and in the anhydrous state, as follows:

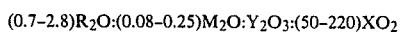

$$(0.7-2.8)R_2O:(0.08-0.25)M_2O:Y_2O_3:(50-220)XO_2$$

wherein R is a nitrogen-containing organic cation, such as, for example, that derived from pyrrolidine, M is an alkali metal cation, especially sodium, and X and Y are as described above, particularly where X is silicon and Y is aluminum.

The original cations of the as-synthesized ZSM-23 can be replaced in accordance with techniques well known in the art, at least in part, by ion exchange with other cations. Preferred replacing cations include metal ions, ammonium ions, hydrogen ions and mixtures thereof. Particularly preferred cations are those which render the zeolite catalytically active especially for hydrocarbon conversion. These include hydrogen, rare earth metals, metals of Groups IIA, IIIB, IVB, VIII, IB, IIB, IIIA, and IVA.

The synthetic ZSM-23 zeolite possesses a definite distinguishing crystalline structure whose X-ray diffraction pattern shows substantially the significant lines set forth in Table I.

TABLE I

| d(A) | I/I$_o$ |
|---|---|
| 11.2 ± 0.23 | Medium |
| 10.1 ± 0.20 | Weak |
| 7.87 ± 0.15 | Weak |
| 5.59 ± 0.10 | Weak |
| 5.06 ± 0.10 | Weak |
| 4.50 ± 0.10 | Weak |
| 4.53 ± 0.10 | Strong |
| 3.50 ± 0.08 | Very Strong |
| 3.72 ± 0.08 | Very Strong |
| 3.62 ± 0.07 | Very Strong |
| 3.54 ± 0.07 | Medium |
| 3.44 ± 0.07 | Strong |
| 3.36 ± 0.07 | Weak |
| 3.16 ± 0.07 | Weak |
| 3.05 ± 0.06 | Weak |
| 2.99 ± 0.06 | Weak |
| 2.85 ± 0.06 | Weak |
| 2.54 ± 0.05 | Medium |
| 2.47 ± 0.05 | Weak |
| 2.40 ± 0.05 | Weak |
| 2.34 ± 0.05 | Weak |

These values were determined by standard techniques. The radiation was the K-alpha doublet of copper, and a scintillation counter spectrometer with a strip chart pen recorder was used. The peak heights, I, and the positions as a function of 2 times theta, where theta is the Bragg angle, were read from the spectrometer chart. From these, the relative intensities, 100 I/I$_o$, where I$_o$ is the intensity of the strongest line or peak, and d (obs.), the interplanar spacing in Angstrom units, corresponding to the recorded lines, were calculated. It should be understood that this X-ray diffraction pattern is characteristic of all the species of ZSM-23 compositions. Ion exchange of the sodium ion with cations reveals substantially the same pattern with some minor shifts in interplanar spacing and variation in relative intensity. Other minor variations can occur depending on the silicon to aluminum ratio of the particular sample, as well as if it has previously been subjected to thermal treatment.

Synthetic ZSM-23 zeolites can be used either in the alkali metal containing form, the alkali metal and/or hydrogen form or univalent or multivalent cationic form. They can also be used in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Combinations of the aforenoted metals may also be used. Such components can be exchanged or cocrystallized into the composition, impregnated thereon or physically intimately admixed therewith. Such components can be impregnated in or onto ZSM-23 such as, for example, by, in the case of platinum, treating the zeolite with a platinum metal-containing ion. Thus, suitable platinum compounds for this purpose include chloroplatinic acid, platinous chloride and various compounds containing the platinum amine complex. Combinations of metals and methods for their introduction can also be used.

As prepared, R can be a cation derived from pyrrolidine present in a quantity not less than 50 percent of the cation content.

M can be one or more or a variety of alkali metal cations, suitably defined as including all alkali metal ions derived from alkali metal oxide or hydroxide as well as alkali metal ions included in alkali metal silicates and aluminates (not including alkali metal salts such as sodium chloride or sodium sulfate which may be derived from neutralization of added inorganic acids such as HCl or $H_2SO_4$ or acid salts such as $Al_2(SO_4)_3$). Non-limiting examples of such suitable alkali meal ions include sodium and potassium.

Synthetic ZSM-23, when employed either as an adsorbent or as a catalyst in a hydrocarbon conversion process, should be dehydrated at least partially. This can be done by thermal treatment, i.e. heating, to a temperature in the range of 50° C. to about 900° C. in an inert temperature, such as air, nitrogen, etc. and at atmospheric or subatmospheric pressures for between 1 and 48 hours. Dehydration can also be performed at lower temperature merely by placing the catalyst in a vacuum, but a longer time is required to obtain a sufficient amount of dehydration.

Zeolite ZSM-23 can be conventionally prepared by preparing a solution containing sources of an alkali metal oxide, preferably sodium oxide, sources of nitrogen-containing cation, preferably pyrrolidine, an oxide of Y as defined above, an oxide of X as defined above, and water, having a composition in terms of mole ratios of oxides, falling within the following ranges:

| | | | |
|---|---|---|---|
| $R^+/(R^+ + M^+)$ | 0.25–0.95 | preferably | 0.40–0.70 |
| $OH/XO_2$ | 0.01–0.5 | preferably | 0.03–0.2 |
| $H_2O/OH$ | 100–2000 | preferably | 200–600 |
| $XO_2/Y_2O_3$ | 12–1000 | preferably | 50–250 | wherein R is an organic nitrogen-containing cation and M is an alkali metal ion, and maintaining the mixture until crystals of the zeolite are formed. (The quantity of $OH^-$ is calculated only from the inorganic sources of alkali without any organic base contribution). Thereafter, the crystals are separated from the liquid and recovered. Typical reaction conditions are set out below:

| | | | |
|---|---|---|---|
| Temperature | 121–204° C. (250–400° F.) | preferably | 149–191° C. (300–375° F.) |
| Time | 10–200 hrs. | preferably | 16 to 100 hrs. |

The digestion of the gel particles is carried out until crystals form. The solid product is separated from the reaction medium, as by cooling the whole to room temperature, filtering and water washing.

The crystalline product is dried, e.g. at 110° C. (230° F.), for from about 8 to 24 hours. Of course, milder conditions may be employed if desired, e.g. room temperature under vacuum.

The composition for the synthesis of synthetic ZSM-23 can be prepared utilizing materials which can supply the appropriate oxide. For aluminosilicates, such compositions include aluminates, alumina, silicates, silica hydrosol, silica gel, silicic acid and hydroxides. It will be understood that each oxide component utilized in the reaction mixture for preparing ZSM-23 can be supplied by one or more essential reactants and they can be mixed together in any order. For example, any oxide can be supplied by an aqueous solution, sodium hydroxide or by an aqueous solution of a suitable silicate; the cation derived from pyrrolidine can be either supplied by pyrrolidine or a salt thereof. The reaction mixture can be prepared either batchwise or continuously. Crystal size and crystallization time of the ZSM-23 composition will vary with the nature of the reaction mixture employed.

Further information relating to ZSM-23 and examples of its conventional preparation from colloidal silica can be found in U.S. Pat. No. 4,076,842 incorporated herein by reference.

DESCRIPTION OF THE PREFERRED EMBODIMENTS

For the alkylation process of this invention, if desired, the ZSM-23 zeolite catalyst can be employed in combination with a support or binder material such as, for example, a porous inorganic oxide support or a clay binder. Non-limiting examples of such binder materials include alumina, zirconia, silica, magnesia, thoria, titania, boria and combinations thereof, generally in the form of dried inorganic oxide gels and gelatinous precipitates. Suitable clay materials include, by way of example, bentonite and kieselguhr. The relative proportion of crystalline aluminosilicate ZSM-23 zeolite of the total composition of catalyst and binder or support may vary widely with the ZSM-23 content ranging from between about 1 to about 99 percent by weight and more usually in the range of about 5 to about 80 percent by weight of the composition.

Exemplary of the hydrocarbons which may be alkylated by the process of this invention are aromatic compounds such as benzenes, naphthalenes, anthracenes, and the like and substituted derivatives thereof; and alkyl substituted aromatics, e.g. toluene, xylene, and homologs thereof. In addition, other non-polar substituent groups may also be attached to the aromatic ring including, by way of example:
Methyl ($—CH_3$)
Ethyl ($—C_2H_5$)
Tert-butyl ($—C(CH_3)_3$)
Alkyl ($—C_nH_{(2n+1)}$)
Cycloalkyl ($—C_nH_{(2n+1)}$)
Phenyl ($C_6H_5$)
Naphthyl ($C_{10}H_7$) and
Aryl (any aromatic radical)

In accordance with this invention, the preferred alkylating agents are $C_2$ to $C_{20}$ olefins such as ethylene, propylene, dodecylene, as well as formaldehyde, alkyl halides and alcohols; the alkyl portion thereof having from 1 to 24 carbon atoms. Numerous other acyclic compounds having at least one reactive alkyl radical may be utilized as alkylating agents.

The process of the present invention comprises contacting a hydrocarbon charge in a reaction zone with an alkylating agent under alkylation conditions in the presence of ZSM-23 zeolite catalyst. Operating conditions employed in the process of the present invention are dependent, at least in part, on the specific alkylation reaction being effected. Such conditions as temperature, pressure, space velocity and molar ratio of the reactants and the presence of inert diluents will have some effect on the process. Accordingly, the manner in which these conditions affect not only the conversion and distribution of the resulting alkylated products but also the rate of deactivation of the catalyst will be described below.

The process of this invention is conducted such that alkylation of an aromatic hydrocarbon compound, exemplified by benzene, with an alkylating agent, such as an olefin, exemplified by ethylene, can be carried out in the vapor-phase by contact in a reaction zone, such as, for example, a fixed bed of catalyst, under alkylation effective conditions, said catalyst being characterized as the above-defined ZSM-23 which has been hydrogen exchanged such that a predominate portion of its exchangeable cations are hydrogen ions. In general, it is contemplated that more than 50 percent and preferably more than 75 percent of the cationic sites of the ZSM-23 zeolite will be occupied by hydrogen ions. Any number of stages may be employed in the reaction zone within the range of about 1 to 10, preferably about 2 to 8. The alkylatable aromatic compound and alkylating agent are desirably fed to a first stage at an appropriate mole ratio of one to the other. The feed to such first stage is heated. After some reaction takes place, such as, for example, when about 80 percent of the alkylating agent is consumed, the effluent of the first stage is cooled to remove heat of reaction and more alkylating agent is added (second stage) to maintain the mole ratio of aromatic compound to alkylating agent within the range established for the first stage. It is generally desirable to provide cooling between reactor stages.

Considering vapor-phase alkylation of benzene with ethylene, the first stage mole ratio of benzene to ethylene may be in the range of about 1:1 to about 60:1. The first stage feed is heated to a reactor inlet temperature within the range of about 343° C. (650° F.) to about 482° C. (900° F.) at a pressure within the range of about 4 to about 3000 psig. Inlet temperatures may fall within the range of about 371° C. (700° F.) to about 459° C. (850° F.) and pressures may fall within the range of about 25 psig to about 450 psig. The repeating of reaction staging can be carried out while maintaining an overall aromatic hydrocarbon, e.g. benzene, to alkylating agent, e.g. ethylene, mole ratio of about 1:1 to about 60:1, with a preferred range of about 2.5:1 to about 30:1, e.g. about 10:1. As the reaction proceeds through the stages, the aromatic:alkylating agent mole ratio increases.

It is noted that extremely high total feed space velocities are possible in the process of this invention, i.e. up to 200 lb. total feed/hr.-lb. crystalline zeolite. An important factor in the present process is, however, the weight hourly space velocity (WHSV) of the alkylating agent, e.g. ethylene. The alkylating agent WHSV to each of any alkylation reactor stages can be maintained between about 1 and about 10 lb. alkylating agent/hr.-lb. crystalline zeolite. In particular, the WHSV of the alkylating agent may be maintained within the range of about 2 to about 8 lb. ethylene/hr.-lb. crystalline zeolite. When the ethylene WHSV is maintained within the above limits, an economical cycle between regenerations of catalyst exists. WHSV with respect to the alkylated material, e.g. benzene, is about 0.1 to 450, preferably about 0.5 to 300.

Although conventionally prepared ZSM-23 exhibits sufficient selectivity such as to prevent excessive formation of undesired residues by transalkylation, the activity of such catalysts may be less than that desired. While not wishing to be bound by theory, it is nonetheless believed that pore obstruction by silica tends to reduce the activity of such catalysts. A particularly preferred embodiment of the present invention utilizes a type of ZSM-23 whose pores are substantially unobstructed by silica. Such material exhibits significantly increased activity in the alkylation of aromatic hydrocarbons. ZSM-23 whose pores are substantially unobstructed by silica may be prepared from a forming mixture which contains amorphous precipitated silica as the silica source. Commonly assigned U.S. Application Ser. No. 509,671, filed June 30, 1983, and now abandoned, discloses such preparation of zeolites from forming mixtures of high solids content. Because ZSM-23 made from forming mixtures containing amorphous precipitated silica has been found to be relatively free of silica obstruction in its pores, it is believed that the activity of such ZSM-23 zeolite is greater than one made according to conventional methods wherein the forming mixture is, say, a silica hydrogel.

ZSM-23 which is utilized in this particularly preferred embodiment is prepared from a forming mixture containing sources of silica, alkali metal, and water, wherein precipitated silica is used as a silica source. Upon mixing, a non-gel forming mixture having a solids content greater than about 5 percent, say, ranging from about 7 to 25 percent is produced. The precipitated silica may range in particle size from 0.01 to 100 microns, and may preferably have an average particle size of about 0.02 microns.

The amorphous precipitated silica suitable for producing high activity ZSM-23 zeolite can be a synthetic wet-process, hydrated amorphous silica having a particle size range of about 0.01 to 100 microns, containing trace impurities of $Al_2O_3$ and NaCl. Preferably, the particles are of a spherical shape with an average diameter of about 0.02 microns. These particles tend to agglomerate in loose "grape cluster" structures. The precipitated silicas used to form the particularly preferred ZSM-23 used in the present invention generally have an unusually large surface area ranging from about 140 to 160 square meters per gram. Hi-Sil, a product of PPG Industries Chemical Division, FK-320, available from Degussa Corporation, QUSO from PQ Corporation, and ZEOFREE-80 manufactured by J. M. Huber Corporation, have all been found suitable for producing ZSM-23 having significantly reduced silica pore occlusion.

The substitution of amorphous precipitated silica such as Hi-Sil for conventional sources of silica, such as sodium silicate, may be practiced in a wide variety of highly siliceous zeolite syntheses. Generally, ZSM-23 zeolites having a constraint index ranging from about 1 to 12 and a silica to alumina ratio of at least about 12 can be made by preparing a non-gel forming mixture containing sources of silica, alkali metal, and water wherein amorphous precipitated silica is utilized as the silica source. The solids content of this forming mixture is greater than about 5 weight percent.

In addition to sources of silica, alkali metal and water, optional ingredients in the forming mixture include surfactants, alum ($Al_2(SO_4)_3$), sodium chloride as well as ZSM-23 seed crystals.

The following examples will serve to illustrate the process of the invention, without unduly limiting the same.

EXAMPLE I

Preparation of ZSM-23 Having a Silica to Alumina Ratio of 95 From a Forming Mixture Containing Colloidal Silica as a Silica Source A silicate solution was prepared by mixing 105 parts colloidal silica (30% by weight) and 134 parts water. An aluminate solution was prepared by combining 18 parts water, 1 part sodium aluminate, 0.4 parts sodium hydroxide (50% by weight) and 11 parts pyrrolidine. These two solutions were combined with stirring in an autoclave. After approximately 15 minutes 0.5 parts of ZSM-23 crystals (prepared from a previous batch) were added to the solution. The reactants were mixed at room temperature for one hour. The autoclave was heated to 166° C. (330° F.) and maintained at this temperature for 144 hours. The resultant zeolite was then filtered, washed in a Buchner funnel and dried at 121° C. (250° F.). The X-ray diffraction analyses indicated that the zeolite was ZSM-23 and the chemical analysis contained a silica to alumina molar ratio of 95.

The zeolite was mixed with alumina to make a mixture of 65 parts zeolite and 35 parts alumina (by weight). Enough water was added to the mixture so that the resulting catalyst could be formed into 1/16" extrudates. These extrudates were activated by first calcining in nitrogen at 538° C. (1000° F.) followed by aqueous exchanges with ammonium nitrate solution and finally calcining in air at 538° C. (1000° F.).

EXAMPLE II

Preparation of ZSM-23 Having a Silica to Alumina Ratio of 112 From a Forming Mixture Containing Amorphous Precipitated Silica A mixture was prepared by mixing 28.7 parts HiSil 233 (90% silica by weight) with 108 parts water and 4.5 parts sodium chloride. Another mixture was prepared by combining 60 parts water, 1 part aluminum sulfate, 2.8 parts sodium hydroxide (50% by weight) and 8.8 parts pyrrolidine. These two solutions were combined with stirring in an autoclave. After approximately fifteen minutes 1.5 parts of ZSM-23 crystals (prepared from a previous batch) were added to the solution. The reactants were mixed at room temperature for one hour. The autoclave was heated to 160° C. (320° F.) and maintained at this temperature for 64 hours. The resultant zeolite was then filtered, washed in a Buchner funnel and dried overnight at 121° C. (250° F.). The zeolite product was determined to be ZSM-23 having a silica to alumina molar ratio of 112.

The zeolite was mixed with alumina to make a mixture of 65 parts zeolite and 35 parts alumina (by weight). Enough water was added to the mixture so that the resulting catalyst could be formed into 1/16" extrudates. These extrudates were activated by first calcining in nitrogen at 538° C. (1000° F.) followed by aqueous exchanges with ammonium nitrate solution and finally calcining in air at 538° C. (1000° F.).

EXAMPLE III

Preparation of ZSM-23 Having a Silica to Alumina Ratio of 72 From a Forming Mixture Containing Amorphous Precipitated Silica A silica source mixture was prepared by mixing 14.3 parts HiSil 233 (90% silica by weight) with 54 parts water. An aluminum source mixture was prepared by combining 31 parts water, 1 part aluminum sulfate, 0.9 parts sodium hydroxide (50% by weight) and 4.4 parts pyrrolidine. These two solutions were combined with stirring in an autoclave. After mixing for approximately one hour at room temperature, the autoclave was heated to 171° C. (340° F.) and maintained at this temperature for 88 hours. The resulting zeolite was filtered, washed in a Buchner funnel and dried at 121° C. (250° F.). The zeolite product was determined to be ZSM-23 having a silica to alumina molar ratio of 72.

The zeolite was mixed with alumina to make a mixture of 65 parts zeolite and 35 parts alumina (by weight). Enough water was added to the mixture so that the resulting catalyst could be formed into 1/16" extrudates. These extrudates were activated by first calcining in nitrogen at 538° C. (1000° F.) followed by aqueous ammonium nitrate exchanges and a final calcination in air at 538° C. (1000° F.).

EXAMPLE IV

Evaluation of Alkylation Activity of Catalysts from Examples I and II

ZSM-23 catalysts from Examples I and II were evaluated for their activity in promoting the alkylation of benzene with ethylene. The test conditions and results were as follows:

| 1.0 gram of catalyst Charge Stock: | Ethylene and Benzene | |
|---|---|---|
| Benzene/Ethylene Mole Ratio: | 7 | |
| Temperature: | 427° C. (800° F.) | |
| WHSV with respect to ethylene: | 1.3 hr$^{-1}$ | |
| Pressure: | 0 psig | |
| | Catalyst of Ex. I | Catalyst of Ex. II |
| Ethylene Conversion, wt % | 4.9 | 13.3 |
| Ethylbenzene Yield, wt % | 1.1 | 10.7 |

The results indicate that the ZSM-23 of Example II made from a forming mixture containing amorphous precipitated silica as a silica source has a greater activity for alkylation of benzene with ethylene than the catalyst of Example I which was prepared from a forming mixture containing colloidal silica.

EXAMPLE V

Evaluation of Transalkylation Activity of ZSM-23 Catalysts of Examples II and III with ZSM-5 Based Ethylbenzene Catalyst The transalkylation promoting tendencies of catalysts of Examples II and III were compared with those of a ZSM-5 based ethylbenzene catalyst. The ZSM-5 catalyst sample consisted of 1/16 inch extrudates containing 65 parts by weight of HZSM-5 for every 35 parts of alumina.

The following test conditions were employed:
1.0 g Catalyst
Charge Stock: Ethylene and benzene
Benzene/ethylene mole ratio: 7
Temperature: 800° F.
WHSV with respect to ethylene: 1.3 Hr$^{-1}$
Pressure: 0 PSIG The results of the transalkylation activity screening test were as follows:

| | ZSM-23 of Example II | ZSM-23 of Example III | ZSM-5 Commercial Catalyst |
|---|---|---|---|
| Ethylene Conv., Wt % | 13.3 | 21.0 | 22.7 |
| Ethylbenzene Yield, Wt % | 10.68 | 16.79 | 17.94 |
| Diethylbenzene Yield, Wt % | 0.71 | 1.25 | 2.52 |
| Xylene Yield, Wt % | 0.02 | 0.01 | 0.08 |

What is claimed is:

1. A process for effecting alkylation of an aromatic-containing hydrocarbon charge in a reaction zone which comprises contacting said charge with an alkylating agent under conditions effective for accomplishing said alkylation in the presence of ZSM-23 zeolite catalyst whose pores are substantially unobstructed by silica.

2. A process for effecting alkylation of an aromatic-containing hydrocarbon charge in a reaction zone which comprises contacting said charge with an alkylating agent under conditions effective for accomplishing said alkylation, in the presence of ZSM-23 zeolite catalyst which is made from a non-gel forming mixture containing amorphous precipitated silica as a silica source.

3. The process of claim 2 wherein said alkylating agent is an oelfinic hydrocarbon containing from 2 to 20 carbon atoms.

4. The process of claim 2 wherein the zeolite is combined in an amount between about 1 and about 99 weight percent in a binder therefor.

5. The process of claim 4 wherein said binder is alumina.

6. The process of claim 2 wherein said alkylation is effected in the vapor phase, said aromatic hydrocarbon is benzene and wherein said olefinic hydrocarbon alkylating agent is ethylene.

7. The process of claim 2 wherein said zeolite has a silica to alumina ratio of at least about 12.

8. The process of claim 6 wherein the benzene to ethylene mole ratio ranges from about 1 to 60, the temperature ranges from about 343° to 482° C., WHSV ranges from about 1 to 10 $hr^{-1}$, with respect to ethylene, pressure ranges from about 4 to 3000 psig, and any number of stages being employed in the reaction zone within the range of about 1 to 10.

9. The process of claim 8 wherein the benzene to ethylene mole ratio ranges from about 2.5 to 30, the temperature ranges from about 371° to 459° C., WHSV ranges from about 2 to 8 $hr^{-1}$ with respect to ethylene, pressure ranges from about 25 to 450 psig, and any number of stages being employed in the reaction zone within the range of about 2 to 8.

* * * * *

UNITED STATES PATENT AND TRADEMARK OFFICE
CERTIFICATE OF CORRECTION

PATENT NO. : 4,547,605
DATED : October 15, 1985
INVENTOR(S) : Charles T. Kresge et al.

It is certified that error appears in the above-identified patent and that said Letters Patent is hereby corrected as shown below:

Column 3, line 35, should appear as shown below:

-- $(0.58-3.4)M_{2/n}O:Y_2O_3 \geq (10XO_2)$ --.

Signed and Sealed this

Twenty-seventh Day of May 1986

[SEAL]

Attest:

DONALD J. QUIGG

Attesting Officer

Commissioner of Patents and Trademarks